United States Patent [19]

Dorn

[11] Patent Number: 4,518,862
[45] Date of Patent: May 21, 1985

[54] SYSTEM FOR DETECTING THE POSITION OF A SHEET ON ITS SUPPORT

[75] Inventor: Alfred Dorn, Rodgau, Fed. Rep. of Germany

[73] Assignee: M.A.N.-Roland Druckmaschinen Aktiengesellschaft, Del.X

[21] Appl. No.: 417,068

[22] Filed: Sep. 13, 1982

[30] Foreign Application Priority Data

Sep. 4, 1981 [DE] Fed. Rep. of Germany ....... 3135022

[51] Int. Cl.³ .............................................. G01B 11/00
[52] U.S. Cl. .................................... 250/561; 356/375
[58] Field of Search ............... 250/557, 561, 548, 202; 356/375, 394, 400; 382/46, 61; 364/559

[56] References Cited

U.S. PATENT DOCUMENTS

| | | | |
|---|---|---|---|
| 3,621,266 | 11/1971 | Akuta et al. | 356/398 X |
| 4,074,131 | 2/1978 | Schwebel | 456/375 X |
| 4,277,176 | 7/1981 | Grosvernier | 250/561 X |
| 4,367,045 | 1/1983 | Grosvernier | 250/561 X |

FOREIGN PATENT DOCUMENTS 2202087 9/1972 Fed. Rep. of Germany.
2913410 10/1980 Fed. Rep. of Germany.

OTHER PUBLICATIONS

Brochure "CCD Analog VLSI-Technology of the 80's" published by Electronic 2000 Vertriebs GmbH Neumarkter Str. 71 presented at the LASER Exposition in Munich on Jun. 2, 1981, pp. 5-6, 86-89, 126.30-126.32.

Primary Examiner—Edward P. Westin
Attorney, Agent, or Firm—Leydig, Voit, Osann, Mayer & Holt, Ltd.

[57] ABSTRACT

An apparatus for determining the position of a sheet when the sheet is placed on a support having at least two spaced apart CCD linear image sensors recessed in the sheet support and partially covered by the edge portions of the sheet. The CCDs operate as line cameras, and are scanned to generate signals correlated with the points of intersection of the sheet edges and the axes of the image sensors. Preferably the apparatus has circuitry for storing calibration values of the CCD signals obtained when the image sensors are not covered by the sheet, circuitry for storing corresponding scanning signal values when the image sensors are covered by the sheet, circuitry for comparing corresponding calibration and scanning values for obtaining difference values, and circuitry for detecting maxima in the gradient of the difference values for adjacent image points to find the locations of the points of intersection of the sheet edges and the axes of image sensors. These locations are used by software driving an X-Y plotter head or by a sheet positioning mechanism to correct for variations in sheet position.

11 Claims, 9 Drawing Figures fig. 1.

SYSTEM FOR DETECTING THE POSITION OF A SHEET ON ITS SUPPORT

This invention relates to means for detecting the position or orientation of a sheet on a support. If, for example, printing is to start at specific areas of the sheet, the sheet must be in a defined position on its support so that the specific areas will always have the same coordinates. This is especially important when there is already printed matter on the sheet and further printing or measurement operations must be aligned with the pre-printed matter. Moreover, measurement or display of already printed matter on a sheet is often done remote from the printing device or press in order to evaluate the printing process, and for accurate and precise measurements it is desirable to know the precise location of the sheet.

One possible means for determining the position of a sheet on a support would be to use stops against which the sheet could bear so that the sheet would be positioned in a predefined location and orientation. But since stops must project from the support, the area around the stops would not be available for certain measuring or printing devices.

Manual positioning is subject to human error, and is too imprecise for many required measurement operations. Manual positioning is also difficult in remote or obstructed locations.

One previously known method for determining the position of a sheet on its support is disclosed in German Offenlegungsschrift No. 2 913 410. A photoelectric measuring device detects the position of an edge of the sheet on the support with a resolution of at least 0.01 mm. For this purpose, a row or linear array of closely spaced optical fibers are situated in a window in the sheet support opposite a light source. An edge portion of the sheet in proximity with the window has its image projected onto the ends of the optical fibers. Each optical fiber is connected to an evaluator unit which converts the light signal in the fiber to an electrical signal which is subjected to appropriate further processing. A disadvantage of this system, however, is that a special light source must be used and the presence of the light source makes a portion of the sheet inaccessible for measuring purposes.

The general aim of the invention is to provide a means for determining the position of a sheet on its support without using stops so that the support is absolutely flat to insure accuracy and wherein the entire sheet area is accessible for measurement, display, or printing purposes.

Another object of the invention is to provide automatic means for responding to and compensating for a variation in position of a sheet on a support.

A specific object is to provide automatic means for accessing any desired location on a sheet independent of the orientation of the sheet on its support.

Still another object is to provide optical means for determining a position of a sheet on its support that has high resolution but operates without a special light source.

In accordance with the present invention, an apparatus for determining the position of a sheet when the sheet is placed on a support has at least two spaced-apart image sensors afixed to the sheet support, each have a plurality of light sensing points receiving an image of an edge portion of the sheet when the sheet is placed on the support. Preferably high resolution CCD image sensors are used that are disposed in recesses in the sheet support. Electronic means scan the light sensing points of the image sensors along generally linear paths and generate respective electrical signals correlating the received light intensity with the position of the sheet. Edge detecting means convert the respective electrical signals to the coordinates or locations of the intersection of the edges of the sheet and the generally linear path of scanned light sensing points. Preferably the edge detecting means has means for storing calibration values of the signals obtained when the image sensors are not covered by the sheet, means for storing corresponding scanned signal values when the image sensors are covered by the sheet, means for comparing corresponding calibration and scanned values to obtain difference values, and means for detecting maxima in the magnitude of the gradient of the difference values for adjacent image points to find the coordinates or locations of the points of intersection. The coordinates of the points of intersection are used by software driving an X-Y plotter head to correct or compensate for variations in sheet position, or are used to adjust a display.

Other objects and advantages of the present invention will become apparent upon reading the following detailed description and upon reference to the drawings in which.

While the invention is susceptible to various modifications and alternative forms, specific embodiments thereof have been shown by way of example in the drawings and will herein be described in detail. It should be understood, however, that the intention is not to limit the invention to the particular forms disclosed, but, on the contrary, the intention is to cover all modifications, equivalents, and alternatives falling within the spirit and scope of the invention as defined by the appended claims.

Figure 1:
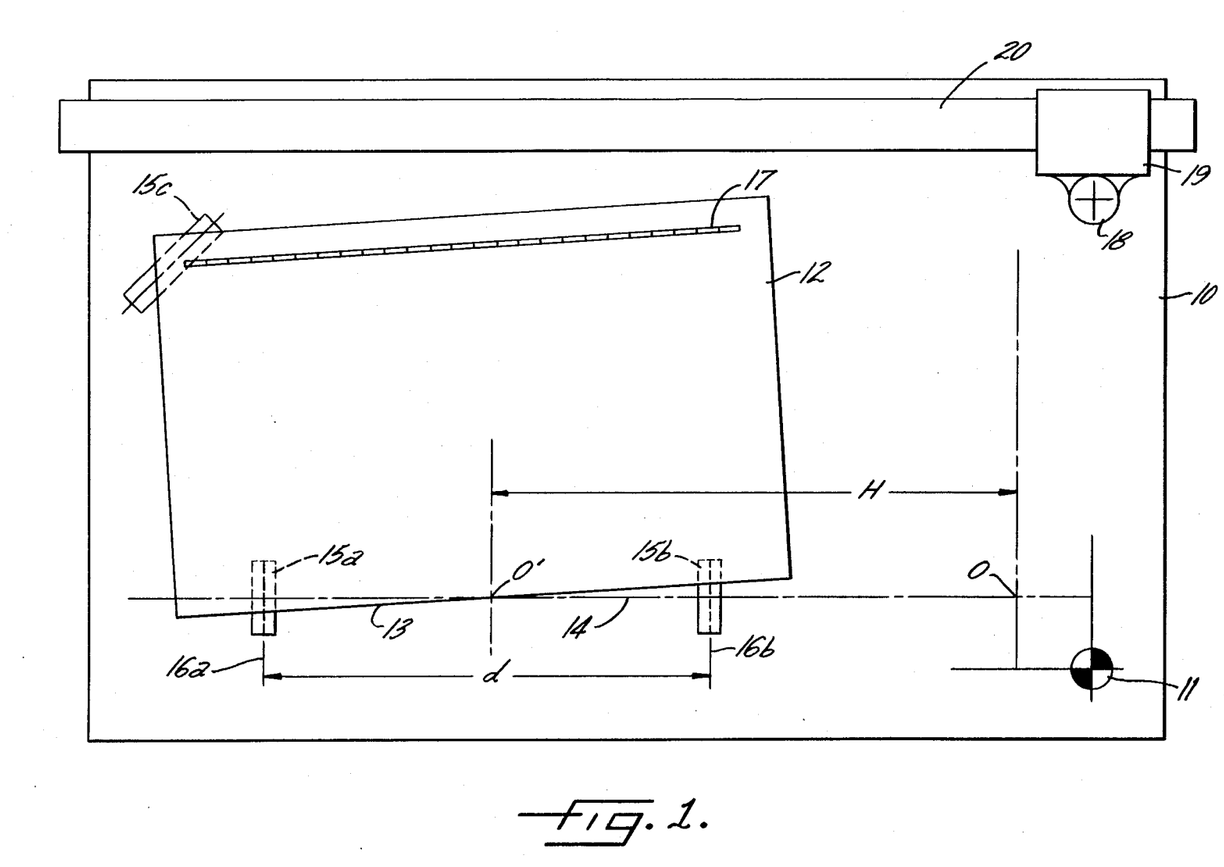
FIG. 1 is a diagrammatic plan view of an embodiment of the invention wherein the head of an X-Y positioning mechanism is driven according to a procedure corrected for variations in the position of a sheet on its support.

Turning now to the drawings, there is shown in FIG. 1 a sheet support 10 comprising the bed of an X-Y plotter or positioning mechanism. The support 10 has a reference point 11 from which all coordinates on the support 10 are referenced, for example during an initial calibration procedure. The support 10 receives a sheet 12 having an edge 13 which is selected as a reference edge. In general, the reference edge 13 will not precisely line up with an imaginary reference line 14, which is horizontal in FIG. 1.

In order to detect the deviation of the edge 13 from the horizontal line 14, a pair of CCD image sensors or "line scan cameras" are spaced apart by a distance d and positioned along the horizontal reference line 14. The image sensors 15a, 15b each have a linear array of light sensing or image points aligned along axes 16a, 16b, respectively, which are shown vertical. Light received at these image points is converted to electrical signals at a plurality of image sensing elements or cells (not shown) inside the image sensors 15a, 15b. The image sensors 15a, 15b are recessed in the sheet support 10 and, as shown in FIG. 1, they are partially covered by the sheet 12 so that a segment of each linear array of light sensing elements in the sensors 15a, 15b is covered while another segment is exposed to ambient light. Hence, the point of intersection of the covering edge 13 of the sheet with the axis of each array is correlated with a maximum gradient along the respective axis in the light intensity received by the respective light sensing element. In other words, the position of the covering edge 13 will fall between two adjacent light sensing elements. The light sensing element being exposed to the ambient light will receive much more light than the light sensing element being covered by the edge portion of the sheet. Hence, the difference or gradient in light received by the exposed element with respect to the light received by the adjacent covered element will be a maximum, compared with the gradients or differences for other adjacent pairs of light sensing elements.

In order to determine the coordinates of the points of intersection of the covering edge 13 with the axes 16a, 16b of the image sensors 15a, 15b, appropriate electronic circuitry, to be described further in detail, scans the light sensing elements and determines the coordinates by processing the multiplexed signals. These coordinates are then used to read or print information on the sheet 12. In one advantageous application, the sheet 12 is a test sheet from a printing press having an ink density strip 17 printed thereon. Since the test strip 17 is printed on production sheets as well as test sheets, it is desirable that the test strip be physically narrow. Hence, it is desirable for the mechanism which reads the test strip to know its inclination with respect to the horizontal reference 14 of the support 10. The actual reading of the test strip 17 is done by an optical densitometer 18 mounted on an X-Y positioning head 19 which travels horizontally across a cross bar 20. Since the cross bar 20 moves vertically, the optical densitometer 18 can move to any coordinates on the support 10.

Persons skilled in the art will recognize that the sheet support 10, head 19 and cross bar 20 are components of commercially available digitally-driven X-Y flat-bed plotters. The plotter is interfaced to a numerical computer by known methods so that the numerical computer will drive the cross head 19 to any desired coordinates as specified by a procedure executed by the numerical computer. The procedure specifies coordinates referenced to an origin 0 in FIG. 1. The angular inclination of the sheet 12 may be referenced to an origin 0' equidistant from the image sensors 15a, 15b at a horizontal distance H from the plotter origin 0. If the points of intersection of the overlapping sheet edge 13 with the axes 16a 16b of the image sensors 15a, 15b are offset from the horizontal reference 14 by vertical displacements EA and EB respectively, then the sheet 12 has a net vertical displacement V' and net angular rotation $\phi$ about 0' according to:

$$V' = (EA + EB)/2$$

$$\phi = \arctan((EB - EA)/d)$$

From these displacements V' and $\phi$ the desired coordinates X, Y may be transformed to new coordinates referenced to the paper 12 to correct for variations and sheet position. If the origin 0' is located, for example, at coordinates (h,v) referenced to the origin 0, then the required coordinate transformations are:

$$X' = (X-h) \cos \phi + (Y-v) \sin \phi + h$$

$$Y' = -(X-h) \sin \phi + (Y-v) \cos \phi + v + V'$$

Thus, by using two sensors spaced horizontally and overlapped by a horizontal edge portion of the sheet, angular and vertical displacements can be detected and corrected. Similarly, if one or more additional sensors are overlapped by a vertical edge portion, then the horizontal displacement of the sheet can be detected and corrected. A particularly advantageous orientation is that of the image sensor 15c in FIG. 1, having light sensing elements partially covered by both a longitudinal and a transverse edge portion of the sheet when the sheet is placed on the support. Then one sensor can locate two different, perpendicular sheet edges.

Figure 2:
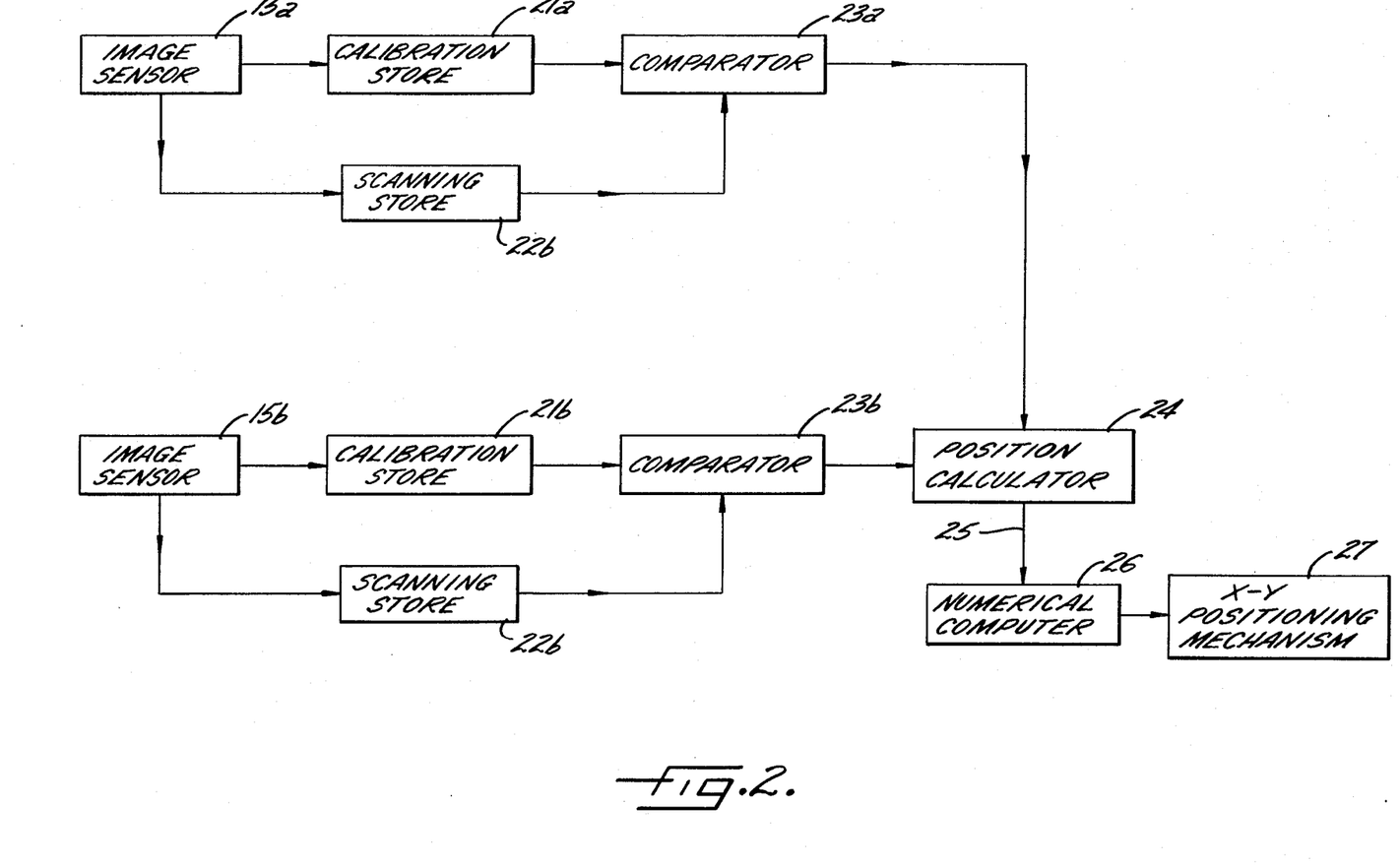
FIG. 2 is a block schematic diagram of the embodiment of the invention shown in FIG. 1.

Shown in FIG. 2 is a block diagram for the edge-detecting electronics which processes the multiplexed electronic signals from the image sensors in order to determine the coordinates of the intersection of the overlapping sheet edge 13 and the image sensor axes 16a, 16b. During an initial calibration step, the image sensors 15a, 15b are uncovered and exposed to ambient light to deliver to respective calibration storage 21a, 21b measured values of the ambient light for each of the light sensing elements in their respective image sensors 15a, 15b. After the calibration step, the sheet 12 is placed on the support 10 and positioned so that the image sensors 15a, 15b are partially covered, as shown in FIG. 1. Then during a position checking step, light intensity values generated by the light sensing elements of the image sensors 15a, 15b are fed to temporary scanning storage 22b. Subsequently, the values are compared with the respective corresponding values in the calibration storage 21a, 21b by respective comparators 23a, 23b. The comparators, for example, calculate the difference between the respective measured values of light intensity stored in the calibration storage 21a, 21b with respective corresponding values stored in the scanning storage 22a, 22b to generate corresponding difference values. The difference values corresponding to the uncovered light sensing elements, for example, would all be approximately zero, regardless of any positional variation in ambient illumination. Thus the difference values generated by the comparators 23a, 23b are indictative of whether their respective corresponding sensing elements are covered by the sheet relatively independent of the magnitude of the response of the individual light sensing elements. In other words, by computing difference values, any variation in value due to uneven response of the light sensing elements to ambient illumination is suppressed.

The difference values are then fed to a position calculator 24 which detects the points of intersection of the covering edge 13 with the image sensor axes by analysis of the variations in the difference values corresponding to different light sensing elements. In a particular embodiment, the position calculator 24 has means for computing the gradient of the difference values for adjacent image points and for detecting maxima in the magnitude of the gradient to indicate the points of intersection.

Also shown in FIG. 2 are the numerical computer 26 and the X-Y positioning mechanism 27, which are standard commercial items.

Figure 3:
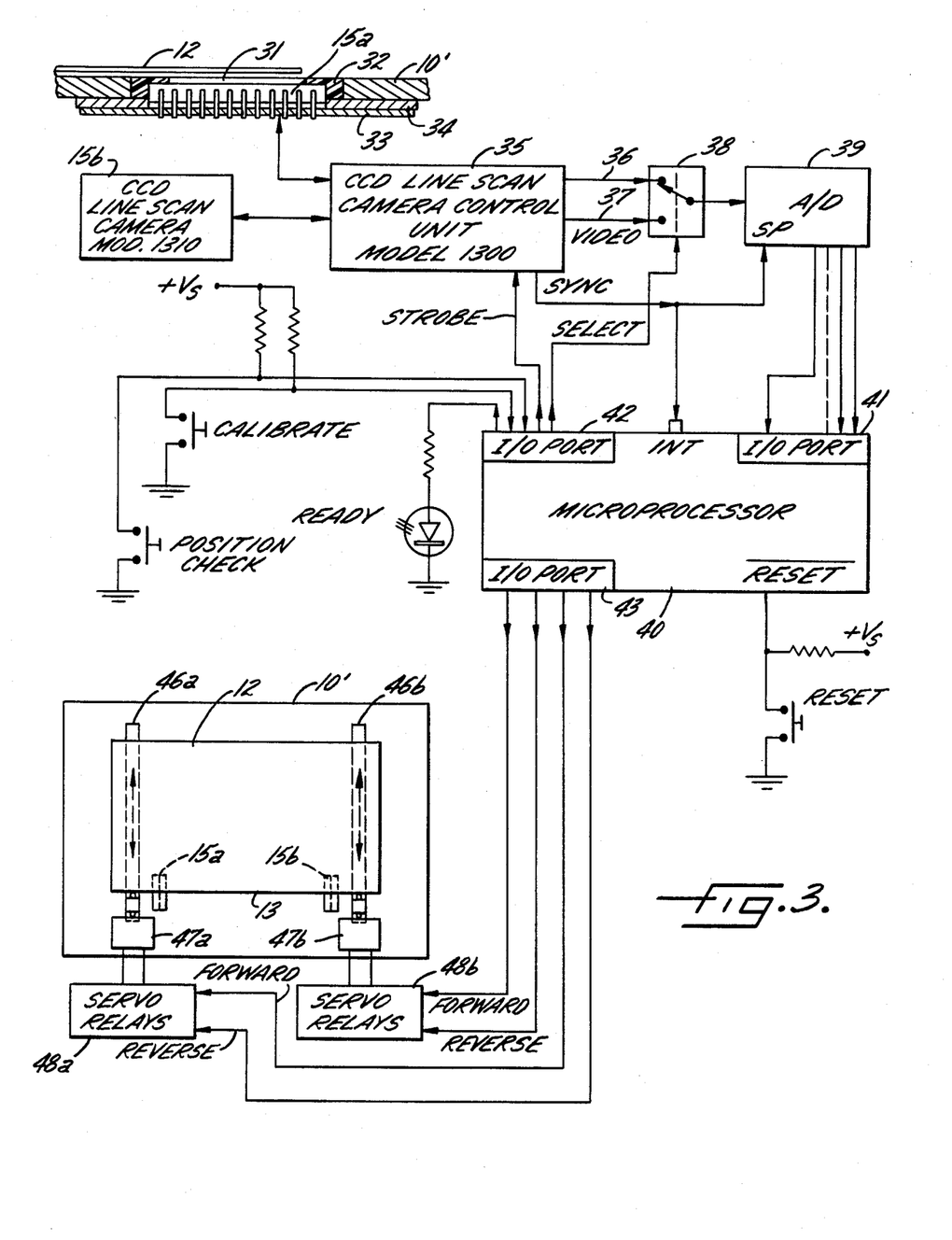
FIG. 3 is an electronic schematic diagram for another embodiment of the invention wherein a sheet positioning mechanism corrects for variations in sheet position.
Figure 4:
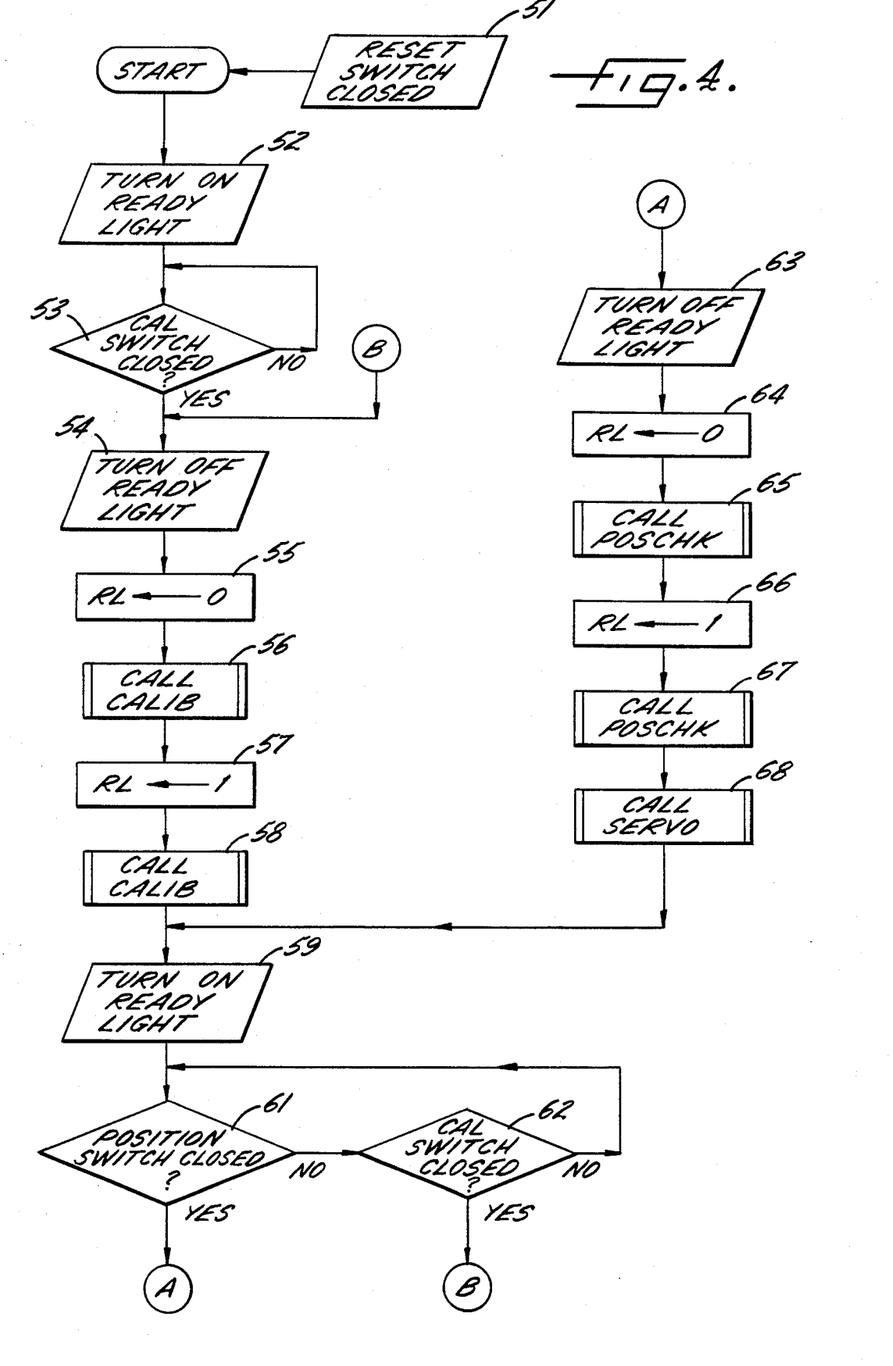
FIG. 4 is a flowchart of an executive procedure for the microprocessor in FIG. 3.

A particular embodiment for the edge-detecting electronics of FIG. 2 is shown in FIG. 3. The embodiment in FIG. 3 determines the sheet position and adjusts the display of the sheet in response to the determined sheet position. In order that the surface of the support 10' is perfectly flat to receive the sheet 12, the top surfaces of the optical windows 31 of the image sensors 15a, 15b are mounted flush with the surface of the support 10'. The integrated circuit 15a, for example, is surrounded by epoxy 32 or a plastic bezel to fill the gap between the integrated circuit 15a and the support 10'. The integrated circuit 15a is further mounted on a printed circuit board 33 that is firmly attached to the support 10' via a spacer 34. Suitable image sensors 15a, 15b are CCD line scan cameras model 1310 manufactured by Fairchild Corporation The image sensing elements or cells in the integrated circuits 15a, 15b are scanned by a line scan camera control unit 35, model 1300 by Fairchild Corporation. In response to a strobe signal, the camera control unit 35 sequentially scans the image sensing elements to generate multiplexed video signals, the scanning being synchronous with a periodic signal SYNC available from the line scan camera control unit 35. Although a separate line scan camera control unit could be used with each image sensor 15a, 15b, electronic circuitry can be saved by paralleling the control inputs to the image sensors 15a, 15b and de-multiplexing the two video outputs on lines 36, 37 using a multiplexer or analog switch 38.

The video signals are analog and are converted to measured values or samples coincident with the sychronization signal SYNC using an analog-to-digital converter A/D 39. Thus, there is a correspondence between samples and image sensing elements, but there need not be a strict one-to-one correspondence. The A/D converter 39 serves as a means for converting the electrical video signals to measured values, the measured values being representative of and corresponding to the electrical signals generated by the respective light sensing elements.

These measured digital values are read by a microprocessor 40 on its I/O port 41, in response to the synchronization signal SYNC on its interrupt input INT. The microprocessor 40 also receives a CALIBRATE switch signal and a POSITION CHECK switch signal, and outputs a READY signal, the STROBE signal to the camera control unit 35, and a SELECT signal to the multiplexer 38 via the I/O port 42.

In order for the microprocessor 40 to adjust the display position of the sheet 12 on the support 10', adjusting fingers 46a, 46b recessed into the support 10' are actuated by servos 47a, 47b. The fingers 46a, 46b tend to translate the sheet 12 along directions parallel to the axes of the image sensors 15a, 15b when the servos 47a, 47b are activated. The microprocessor 40 activates the servos by generating FORWARD and REVERSE enabling signals on its I/O port 43 which energize the servo relays 48a, 48b.

In order for the microprocessor to determine the position of the sheet 12 and to move the sheet 12 to a desired position on the support 10', the microprocessor 40 executes a procedure or series of instructions summarized by the flowcharts in FIGS. 4–9. The microprocessor 40 starts executing an executive procedure shown in FIG. 4 whenever the RESET switch of FIG. 3 is closed, as indicated in step 51 of FIG. 4. The microprocessor responds by turning on the READY light as shown in step 52. If the CALIBRATE push button is closed as tested in step 53, then the READY light is turned off in step 54, the left image sensor 15a is selected by setting the RL flag to 0 in step 55, and calibration values for the left image sensor are determined by the calibration subroutine in step 56. The calibration values for the right image sensor 15b are also measured by setting the RL flag to 1 in step 57 and again calling the calibration subroutine in step 58. In practice, this calibration sequence is initiated by the operator pushing the CALIBRATE switch before a sheet 12 is placed on the support 10'. When the calibration is finished, the microprocessor turns the READY light back on in step 59 and waits for a new command by testing whether the POSITION switch is closed in step 61 and also testing whether the CALIBRATE switch is closed in step 62. If step 62 indicates that the calibration subroutine must be repeated, the execution jumps back to step 54 via the on-page connector B. If the POSITION switch is closed as detected in step 61, the execution jumps via the on-page connector A to step 63 to turn off the READY light and then to perform the position checking and servo driving procedures. Thus, in step 64 the image sensor flag RL is set to 0 to select the left image sensor 15a and the coordinates of the intersection of the overlapping edge 13 of the sheet with the axis of the image sensor 15a is determined by the position checking subroutine POSCHK in step 65. Similarly, the point of intersection for the right image sensor 15b is detected by the microprocessor performing steps 66 and 67. Since the two points of intersection are now known, the servos 46a, 46b may be actuated by a subroutine SERVO in step 68 to move the sheet 12 to a desired position or orientation. Finally, the READY light is turned on in step 59 to signal to the operator that another positioning or calibration operation may be performed.

Figure 5:
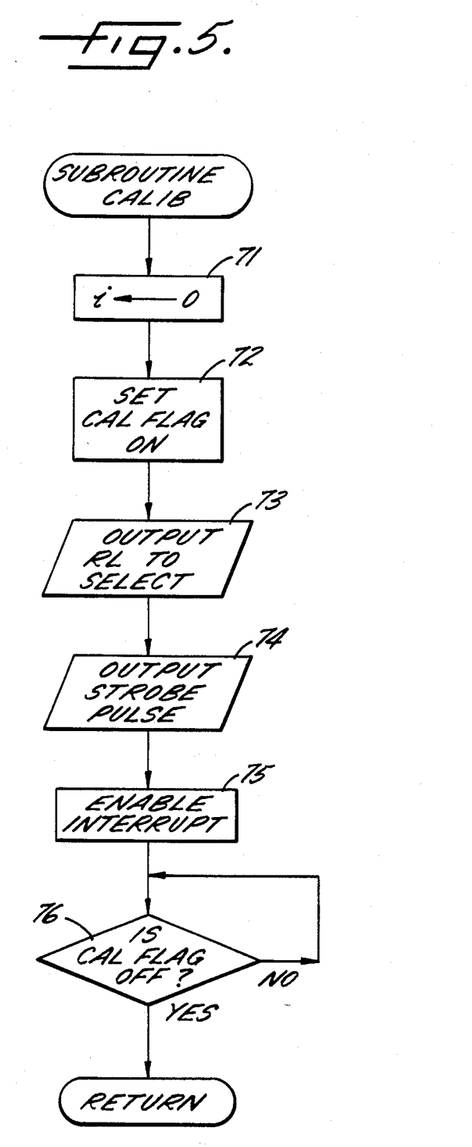
FIG. 5 is a flowchart for a calibration subroutine executed by the microprocessor in FIG. 3 to store calibration values.

The calibration subroutine CALIB which receives and stores measured values from the image sensors when the sheet is not placed on the support, is shown in FIG. 5. The actual calibration values are stored in a two-dimensional array C(i,RL) in the random access memory, or RAM of the microprocessor 40. In the first step 71 of the calibration subroutine, the index i is set to 0 so that the measured values will be stored at the beginning of the array C(i,RL). Then in step 72 the flag CAL is set on. The flag CAL is used to handshake with the interrupt routine so that the calibration subroutine CALIB knows when the interrupt routine has completed its requested function, as will be described later in conjunction with FIG. 7. Then in step 73 the image sensor selecting flag RL is outputed via port 42 to the SELECT line of the multiplexer 38 to select a particular one of the image sensors 15a, 15b. Once a particular image sensor is selected, a pulse is outputed on the STROBE line in step 74 so that the camera control unit 35 will dump the electrical signals generated by the light sensing elements of the selected image sensor and will generate the signal SYNC synchronized to the dumping of the individual light sensing elements onto the video lines 36 and 37 in FIG. 3. Then the interrupt routine is enabled in step 75 so that it may read in the measured values provided by the analog to digital converter A/D 39. The CAL flag is tested in step 76 to determine whether the interrupt routine is finished and has set the CAL flag off. If the CAL flag is off, the calibration subroutine is finished and execution returns to the calling executive program in FIG. 4.

Figure 6:
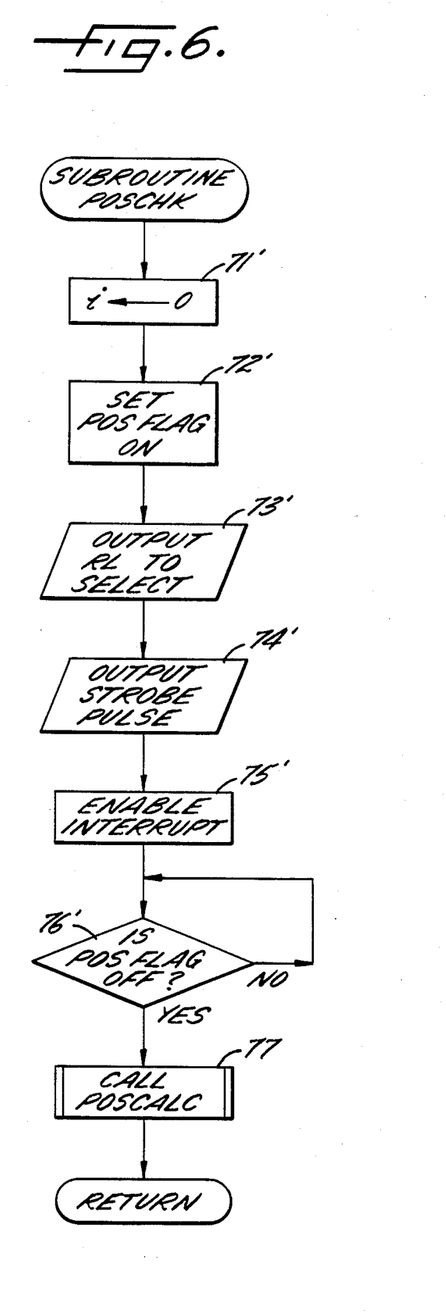
FIG. 6 is a flowchart of a position checking subroutine for temporarily storing scanned values and passing them to a comparing and position calculating subroutine.

The position checking subroutine POSCHK is shown in FIG. 6. Steps 71'-76' perform operations similar to steps 71-76 in the calibration subroutine CALIB of FIG. 5, except for the fact that the POS flag is set on in step 72' so that the interrupt routine accepts the measured values from the A/D converter 39 as position check values rather than calibration values. By the time step 77 is reached, the microporcessor RAM memory has calibration values stored in the array C(i,RL) and the position check values stored in the array S(i) so that position calculations may be performed in step 77.

Figures 7, 8:
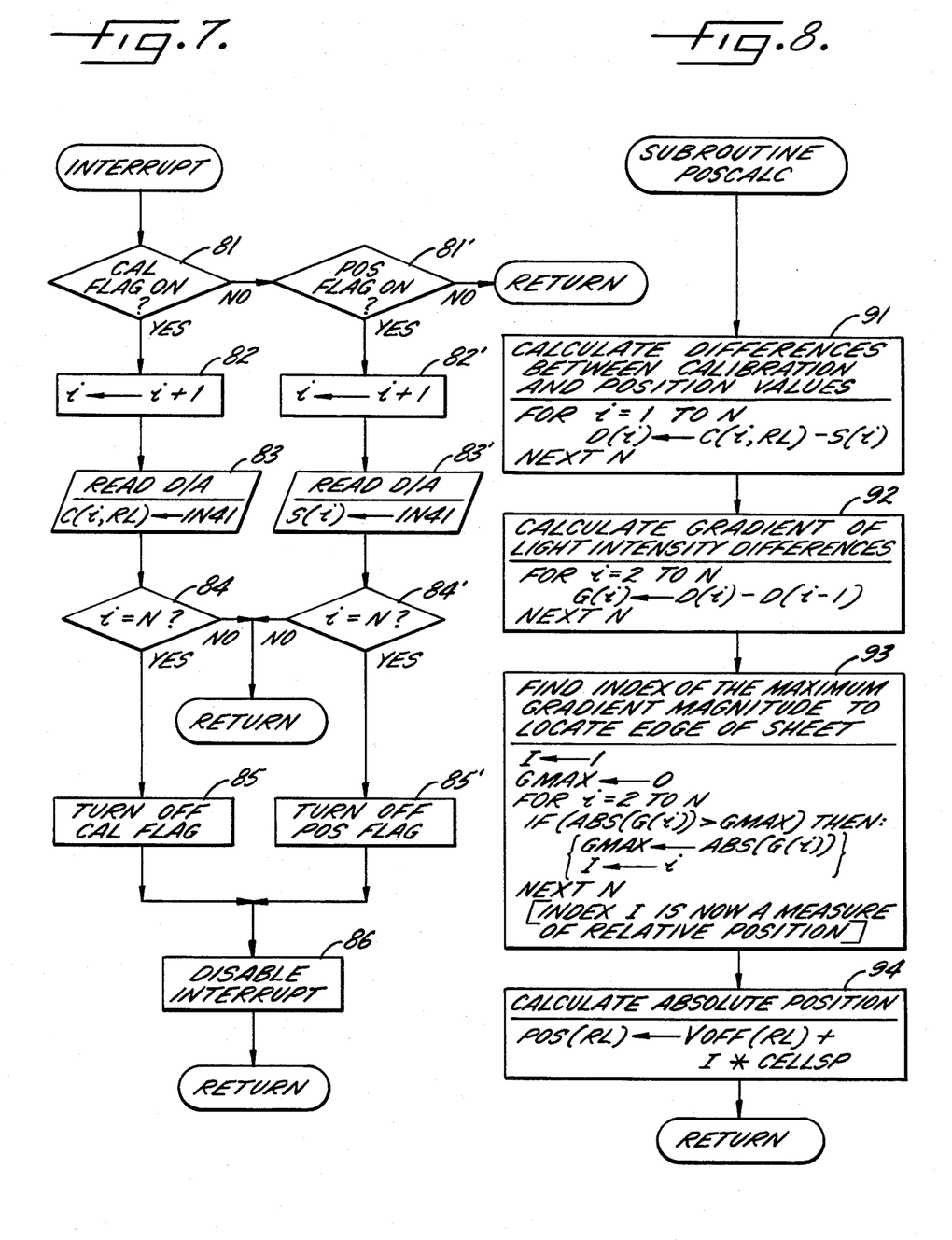
FIG. 7 is a flowchart of an interrupt routine executed by the microprocessor in FIG. 3 to input and store the calibration and scanned values.
FIG. 8 is a flowchart of a comparator and position calculating subroutine executed by the microprocessor in FIG. 3 to calculate the coordinates of the points of intersection of the sheet edges and the axes of the image sensors.

The actual reading in of measured values on the I/O port 41 is performed by an interrupt routine shown in FIG. 7. In the first step 81 the calibration flag CAL is tested and if it is on then the light sensing element pointer i or array index is incremented in step 82. Then the I/O port 41 is read in step 83 and placed in the appropriate calibration array element C(i,RL). In step 84, the index i is compared to the number of light sensing elements N and if the index i is not equal to N, the interrupt routine is finished and execution returns to the foreground routines. But if the index i is equal to N, then all of the light sensing elements have been dumped and their light intensity values measured so that the calibration flag CAL is turned off in step 85 and the interrupt disabled in step 86 to signal to the foreground routines that all of the calibration values have been obtained.

If the calibration flag is off in step 81, then the interrupt routine tests whether the position flag is on in step 81'. If it is, then the position values are read into the position array S(i) in a similar manner as were the calibration values read into the calibration array C(i,RL). Thus the operations performed in steps 81'-85' are analogous to the calibration steps 81-85.

The position calculating subroutine POSCALC is shown in FIG. 8. In step 91, corresponding to the comparators 23a, 23b of FIG. 2, the differences between the respective corresponding calibration and scanned position values are calculated. Then in step 92 the variation or gradient of light intensity differences is calculated. In step 93, the gradient is used to determine the location of the edge of the sheet by finding the maximum gradient GMAX and associating its index I with the position of the overlapping edge 13 of the sheet. In other words, the particular value I of the index i for the maximum gradient magnitude GMAX is a measure of position, the distance unit being directly proportional to the separation between ajacent CCD cells or light sensing elements. (The proportionality depends on the ratio of the cell dumping rate to the A/D sampling rate.) Thus, in step 94, the absolute position of the point of intersection POS(RL) for each respective image sensor 15a, 15b may be calculated by multiplying the particular index I by the effective cell spacing CELLSP and adding on any offset VOFF(RL) due to the positioning of the image sensors 15a, 15b with respect to the sheet support 10'.

As shown and described, the calibration C(i,RL) and position check or scanned values S(i) are determined after one STROBE pulse to the CCD line scan camera circuits 35. Alternatively, as will become evident to persons skilled in the art, several frames of values could be averaged or integrated in the calibration and scanning storage by adding respective corresponding values into the arrays C(i,RL) and S(i,RL) after several individual STROBE pulses. This represents a tradeoff of additional scanning time and storage space for increased signal-to-noise ratio and resolution. It should also be noted that an entire array S(i) instead of a single temporary scanning storage location S has been used in the embodiment shown to simplify programming requirements. Alternatively, all of the calculations in the subroutine POSCALC of FIG. 8 could operate on the single temporary storage location S in serial fashion, instead of using arrays.

Figure 9:
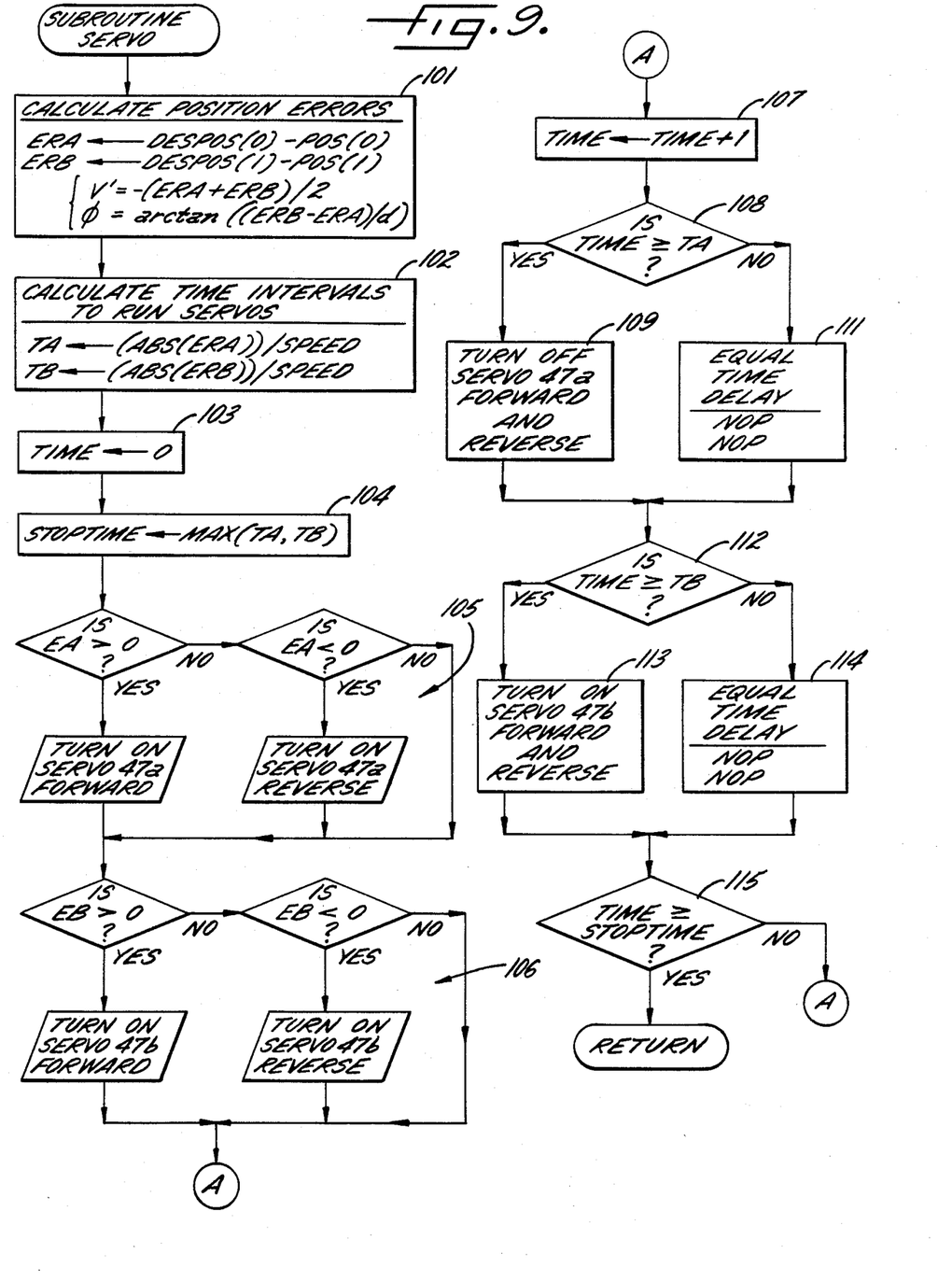
FIG. 9 is a flowchart of a servo driving subroutine executed by the microprocessor in FIG. 3 for driving the sheet positioning servos in FIG. 3 to correct for variations in sheet position.

The sheet positioning subroutine SERVO is shown in FIG. 9. Right and left position errors ERA, ERB are calculated in step 101 by subtracting the respective positions POS(0), POS(1) from the respective desired positions DESPOS(0), DESPOS(1). For the embodiment shown in FIG. 1, these position errors ERA, ERB are used to calculate the vertical offset V' and angle of rotation $\phi$ which are then passed to a coordinate transforming equation as was described above. But for adjusting the sheet position, these errors are used to control servo motors 47a, 47b, as shown in FIG. 3. Since some time is required to determine the position of a sheet, it is desirable to adjust the servos by an amount expected to reduce the errors to zero, so that the error will be reduced to zero iteratively upon successive scans of the sheet position. It should be noted from FIG. 4 that a momentary closure of the POSITION CHECK switch will result in one position check and servo drive cycle. But if this switch is continuously depressed, then the cycle will iterate and the sheet 12 will be moved by the servos 47a, 47b until the position errors ERA, ERB are reduced to zero.

In order to drive the servos so that the error will be reduced approximately to zero, the time for activating the servos is calculated as proportional to the absolute value or magnitude of the respective error divided by the speed of the servos, as shown in step 102. In step 103, a timer TIME is set to 0, and in step 104 a STOP-TIME is calculated as the maximum of the two servo run times TA, TB in step 104. Then each servo is driven for the respective time and in a direction depending upon the sign or polarity of the respective position error. The left servo 47a, for example, is turned on in the steps generally designated 105 while the right servo 47b is turned on in the steps generally designated 106. Then the timer is incremented in step 107. In step 108 the time is compared to the run time for the left servo 47a in step 108, and if the run time has been reached, the servo 47a is turned off in step 109. The delay for turning off the servo in step 109 is equalized by "do nothing" or NOP instructions in step 111. Similarly, the time is compared to the run time for the right servo 47b in step 112 and the servo 47b either turned off in step 113 or the delay equalized in step 114. Finally, the time is compared to the stop time in step 115 to determine if the subroutine SERVO has driven the servos 47a, 47b for their required times.

From the foregoing, a specific apparatus for determining the position of a sheet when the sheet is placed on a support has been disclosed. The position is determined by detecting the extent of covering of high resolution image scanners which are built into the sheet support so that the support is absolutely flat to insure accuracy and so that the entire sheet area is accessible for measurement purposes. The image sensors operate without a special light source, and means are provided for calibrating the response of the sensors to ambient light, and for comparing the calibrated response to the response of the sensors to partial covering of the sheet to correct or equalize the response of the image sensors to the ambient light. In one particular embodiment, means have been disclosed to access any desired location on the sheet independent of the orientation on the sheet on its support.

What is claimed is:

1. An apparatus for determining the position of a sheet when the sheet is placed on a support, comprising, in combination, at least two spaced-apart image sensors affixed to the support and each having a plurality of light sensing points receiving an image of an edge portion of the sheet when the sheet is placed on the support, electronic means for scanning the light sensing points of the image sensors along generally linear paths and generating, for each image sensor, a respective electrical signal correlating received light intensity with the position of the scanned light sensing points, edge detecting means receiving said respective electrical signals for detecting the respective portions of said electrical signals generated by the scanning of the light sensing points receiving the respective images of the edges of the sheet and determining the respective corresponding locations of the light sensing points, so that respective locations of the intersections of the respective sheet edges and the respective scanned paths on the sheet are determined with respect to the support, a digitally-driven X-Y positioning mechanism affixed to the support, and a numerical computer means for driving the head of the X-Y positioning mechanism to selected X, Y coordinates referenced to the support and for solving a coordinate transformation equation for correcting the X, Y coordinates as a function of said respective corresponding locations of the light sensing points determined by the edge detecting means, so that the head of the X-Y positioning mechanism is driven to selected coordinates referenced to the sheet, generally independent of the position of the sheet with respect to the support.

2. The combination as claimed in claim 1 wherein the support and the digitally-driven X-Y positioning mechanism comprise an X-Y flat-bed plotter.

3. The combination as claimed in claim 1 further comprising automatic means for adjusting a display in response to said respective corresponding locations of the light sensing points determined by the edge detecting means.

4. An apparatus for determining the position of a sheet when the sheet is placed on a support, comprising, in combination, at least two spaced-apart image sensors affixed to the support and each having a plurality of light sensing points receiving an image of an edge portion of the sheet when the sheet is placed on the support, electronic means for scanning the light sensing points of the image sensors along generally linear paths and generating, for each image sensor, a respective electrical signal correlating received light intensity with the position of the scanned light sensing points, and edge detecting means receiving said respective electrical signals for detecting the respective portions of said electrical signals generated by the scanning of the light sensing points receiving the respective images of the edges of the sheet and determining the respective corresponding locations of the light sensing points, so that respective locations of the intersections of the respective sheet edges and the respective scanned paths on the sheet are determined, thereby indicating sheet position, wherein at least one of said image sensors is oriented on the support to have its light sensing elements partially covered by both a longitudinal and a transverse edge portion of the sheet when the sheet is placed on the support.

5. The combination as claimed in claim 1, 2, 3 or 4 wherein the image sensors are high-resolution charge-coupled devices (CCDs).

6. An apparatus for determining the position of a sheet when the sheet is placed on a support, comprising, in combination, at least two spaced-apart image sensors disposed in recesses in the sheet support and being partially covered by the sheet when the sheet is placed on the support, said sensors each having a plurality of light sensing elements arranged in a generally linear array, one segment of each array being partially covered by the sheet so that the point of intersection of the covering edge of the sheet with the axis of the array is correlated with the variation along the axis in the light intensity received by the light sensing elements, the light sensing elements generating electrical signals responsive to the received light intensity, means for converting the electrical signal to measured values, the measured values being representative of and corresponding to the electrical signals generated by respective said light sensing elements, calibration storage means for receiving and storing said measured values when the sheet is not placed on the support, the sensors not being covered by the sheet, scanning storage means for receiving and storing said measured values when the sheet is placed on the support, the sensors being partially covered by the sheet, comparator means for comparing measured values stored in the calibration storage means to respective corresponding values stored in the scanning storage means and generating difference values, so that the difference values are indicative of whether their respective corresponding sensing elements are covered by the sheet relatively independent of the magnitude of the response of the individual light sensing elements, position calculator means for detecting the points of intersection of the covering edges of the sheet with the image sensor axis from the variation in the difference values corresponding to different light sensing elements, a digitally-driven X-Y positioning mechanism affixed to the support, and a numerical computer means for driving the head of the X-Y positioning mechanism to selected X, Y coordinates referenced to the support and for solving a coordinate transformation equation for correcting the X, Y coordinates as a function of the points of intersection calculated by the position calculator means, so that the head of the X, Y positioning mechanism is driven to selected coordinates referenced to the sheet, generally independent of the position of the sheet with respect to the support.

7. The combination as claimed in claim 6 wherein the support and the digitally-driven X-Y positioning mechanism comprise an X-Y flat-bed plotter.

8. The combination as claimed in claim 6 further comprising automatic means for adjusting a display in response to the points of intersection calculated by the position calculator.

9. The combination as claimed in claim 6 wherein at least one of said image sensors is oriented on the support to have its light sensing elements partially covered by both a longitudinal and a transverse edge portion of the sheet when the sheet is placed on the support.

10. The combination as claimed in claim 6 wherein the means for converting comprises means for generating the measured values in digital form, the comparator means comprises means for performing an algebraic subtraction between measured values stored in the scanning storage means and the respective corresponding measured values stored in the calibration storage means, and wherein the position calculator means has means for detecting the variation between the difference values corresponding to different respective light sensing elements for determining the point of intersection of the respective covering edge of the sheet with the axis of the respective image sensor.

11. The combination as claimed in claim 6, 7, 8, 9 or 10 wherein the image sensors are high-resolution charge-coupled devices (CCDs).

* * * * *